US012746528B2

(12) United States Patent
Tsuboi et al.

(10) Patent No.: US 12,746,528 B2
(45) Date of Patent: Sep. 29, 2026

(54) DEODORANT COMPOSITION AND DEODORANT ARTICLE

(71) Applicants: TOSOH CORPORATION, Shunan (JP); SAGAMI CHEMICAL RESEARCH INSTITUTE, Ayase (JP)

(72) Inventors: Yuki Tsuboi, Shunan (JP); Ryohei Nakashima, Shunan (JP); Takumu Nakamura, Shunan (JP); Yukinori Sudo, Shunan (JP); Osamu Kobayashi, Ayase (JP); Daichi Omata, Ayase (JP); Marina Fukawa, Ayase (JP)

(73) Assignees: TOSOH CORPORATION, Shunan (JP); SAGAMI CHEMICAL RESEARCH INSTITUTE, Ayase (JP)

( * ) Notice: Subject to any disclaimer, the term of this patent is extended or adjusted under 35 U.S.C. 154(b) by 359 days.

(21) Appl. No.: 18/551,344

(22) PCT Filed: Mar. 24, 2022

(86) PCT No.: PCT/JP2022/013908

§ 371 (c)(1),
(2) Date: Sep. 19, 2023

(87) PCT Pub. No.: WO2022/202984

PCT Pub. Date: Sep. 29, 2022

(65) Prior Publication Data

US 2024/0198314 A1 Jun. 20, 2024

(30) Foreign Application Priority Data

Mar. 26, 2021 (JP) ................................ 2021-054339

(51) Int. Cl.

| | |
|---|---|
| ***A61L 9/014*** | (2006.01) |
| ***A61K 31/695*** | (2006.01) |
| ***B01J 20/10*** | (2006.01) |
| ***B01J 20/22*** | (2006.01) |
| ***B01J 20/28*** | (2006.01) |
| ***B01J 20/32*** | (2006.01) |

(52) U.S. Cl.

CPC ............... *B01J 20/22* (2013.01); *A61L 9/014* (2013.01); *B01J 20/103* (2013.01); *B01J 20/2803* (2013.01); *B01J 20/3204* (2013.01); *B01J 20/3219* (2013.01); *B01J 20/3257* (2013.01); *B01J 20/3293* (2013.01); *A61L 2209/22* (2013.01)

(58) Field of Classification Search

CPC ........................................................ A61L 9/01

See application file for complete search history.

(56) References Cited

U.S. PATENT DOCUMENTS

| | | | |
|---|---|---|---|
| 4,831,011 | A | 5/1989 | Oikawa et al. |
| 5,206,204 | A | 4/1993 | Tsutsumi et al. |
| 5,238,899 | A | 8/1993 | Kadowaki et al. |
| 6,229,062 | B1 | 5/2001 | Mandell et al. |
| 2020/0061225 | A1 | 2/2020 | Sudo et al. |
| 2023/0059218 | A1 | 2/2023 | Sudo |

FOREIGN PATENT DOCUMENTS

| | | | | |
|---|---|---|---|---|
| CN | 110204638 | A | | 9/2019 |
| JP | 62-191040 | A | | 8/1987 |
| JP | 4-180834 | A | | 6/1992 |
| JP | 4-358536 | A | | 12/1992 |
| JP | 11-4879 | A | | 1/1999 |
| JP | 2000-107274 | A | | 4/2000 |
| JP | 2000-218159 | A | | 8/2000 |
| JP | 2002-306582 | A | | 10/2002 |
| JP | 2002-543243 | A | | 12/2002 |
| JP | 2004262941 | A | * | 9/2004 |
| JP | 2009-247419 | A | | 10/2009 |
| JP | 2014-11 4399 | A | | 6/2014 |
| JP | 2018-108360 | A | | 7/2018 |
| JP | 2020-6160 | A | | 1/2020 |
| JP | 2020-6161 | A | | 1/2020 |
| WO | WO 2021/157630 | A1 | | 8/2021 |

OTHER PUBLICATIONS

Grafting of Metallacarboranes onto Self-Assembled Monolayers Deposited on Silicon Wafers, Chem. Asian J., 2012, 7, 277-281 (Year: 2012).*

International Search Report issued Jun. 14, 2022 in PCT/JP2022/013908 filed on Mar. 24, 2022 citing documents 2-5 & 18-28 therein 3 pages.

* cited by examiner

*Primary Examiner* — Bethany P Barham
*Assistant Examiner* — Danielle Johnson
(74) *Attorney, Agent, or Firm* — Oblon, McClelland, Maier & Neustadt, L.L.P.

(57) ABSTRACT

A deodorant composition which can remove aldehydes more effectively than conventional aldehyde scavengers even after rinsing with water or washings is provided. A deodorant composition comprising a support having chemically bonded aminooxyalkyl groups and a binder resin.

12 Claims, No Drawings

DEODORANT COMPOSITION AND DEODORANT ARTICLE

CROSS-REFERENCE TO RELATED APPLICATIONS

The present application is a 35 U.S.C. § 371 national stage patent application of International patent application PCT/JP2022/013908, filed on Mar. 24, 2022, which is based on and claims the benefits of priority to Japanese Application No. 2021-054399, filed on Mar. 26, 2021. The entire contents of all of the above applications are incorporated herein by reference.

TECHNICAL FIELD

The present invention relates to a deodorant composition and a deodorant article.

BACKGROUND ART

Aldehydes such as acetaldehyde and formaldehyde are typical odorous substances in the living environment and can be a source of unpleasant odor even at low concentrations because of their very low detection thresholds. It is known that these aldehydes emitted from synthetic resins or plywood in buildings and automobiles or contained in cigarette smoke are responsible for sick building syndrome and sick car syndrome. Because these aldehydes are suspected to be carcinogenic, and everyday exposure to them is a risk to human health, the Ministry of Health, Labor and Welfare of Japan has set guideline values of concentration levels of acetaldehyde and formaldehyde in indoor air at 0.03 ppm and 0.08 ppm, respectively. Hence, there is a demand for means to remove aldehydes quickly and persistently.

Porous inorganic materials widely used as deodorants such as silica gel and activated carbon cannot remove lower aldehydes having low boiling points such as acetaldehyde and formaldehyde effectively. Therefore, aldehyde scavengers comprising hydrazine derivatives, amines, amino acids or urea derivatives are proposed to remove aldehydes by chemical reaction with aldehydes (Patent Documents 1 to 3).

PRIOR ART DOCUMENTS

Patent Documents

Patent Document 1: JP-A-H04-358536
Patent Document 2: JP-A-H11-4879
Patent Document 3: JP-A-2018-108360

DISCLOSURE OF INVENTION

Technical Problem

The aldehyde scavengers disclosed in Patent Documents 1 to 3 cannot remove aldehydes efficiently enough and are not waterproof enough to withstand rinsing with water or washings without decrease in performance due to dissolution into water when applied onto resin or textile substrates.

Considering the above-mentioned background art, the present invention aims to provide a deodorant composition which can remove aldehydes more effectively than conventional aldehyde scavengers even after rinsing with water or washings.

Solution to Problem

As a result of their extensive research to solve the above-mentioned problem, the present inventors found a particular waterproof deodorant composition and accomplished the present invention.

Namely, the present invention is embodied in the followings.

[1] A deodorant composition comprising a support having chemically bonded aminooxyalkyl groups and a binder resin.

[2] The deodorant composition according to [1], wherein the support having chemically bonded aminooxyalkyl groups has one of the structures represented by the following formula (2):

(2)

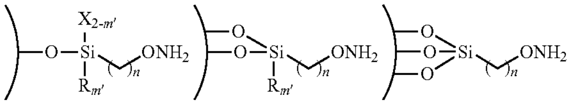

(wherein R is a $C_{1-4}$ alkyl group, X is a $C_{1-4}$ alkoxy group, m' is an integer of from 0 to 2, and n is an integer of from 1 to 12).

[3] The deodorant composition according to [2], wherein R is a methyl group, and X is a methoxy group, an ethoxy group, a propoxy group or an isopropoxy group.

[4] The deodorant composition according to [2], wherein n is 3 or 11.

[5] The deodorant composition according to [1] or [2], wherein the support having chemically bonded aminooxyalkyl groups is a product of a reaction of a compound represented by the following formula (1) with an inorganic support or polymer support having hydroxy groups on the surface:

(1)

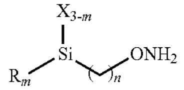

(wherein R is a $C_{1-4}$ alkyl group, X is a $C_{1-4}$ alkoxy group, m is an integer of from 0 to 2, and n is an integer of from 1 to 12).

[6] The deodorant composition according to [5], wherein R is a methyl group, and X is a methoxy group, an ethoxy group, a propoxy group or an isopropoxy group.

[7] The deodorant composition according to [5], wherein n is 3 or 11.

The deodorant composition according to any one of [5] to [7], wherein the inorganic support is silica gel, alumina, zeolite, magnesia, titania, zirconia, ceria, diatomaceous earth, activated carbon, or hydroxyapatite.

[9] The deodorant composition according to any one of [5] to [7], wherein the inorganic support is silica gel.

[10] The deodorant composition according to any one of [1] to [9], wherein the binder resin is an acrylate resin, a silicone resin or a urethan resin.

[11] A method for removing an aldehyde, which comprises exposing the deodorant composition as defined in any one of [1] to [10] to air containing an aldehyde to bring the aldehyde into contact with the deodorant composition.

[12] A deodorant article comprising the deodorant composition as defined in any one of [1] to [10] and a substrate having the deodorant composition on the surface.

[13] The deodorant article according to [12], wherein the substrate is fiber, sheet wallpaper, sponge, beads, wood, plywood or plasterboard.

[14] A method for removing an aldehyde, which comprises exposing the deodorant article as defined in [12] or [13] to air containing an aldehyde to bring the aldehyde into contact with the deodorant article.

Advantageous Effects of Invention

The present invention can provide an aldehyde scavenger which is more waterproof than conventional ones and can remove an aldehyde effectively even after rinsing with water or washings.

DESCRIPTION OF EMBODIMENTS

Now, the present invention will be described in detail.

The deodorant composition of the present invention comprises a support having chemically bonded aminooxyalkyl groups and a binder resin.

The support having chemically bonded aminooxyalkyl groups is not particularly restricted, but may, for example, be a support having one of the structures represented by the formula (2):

(2)

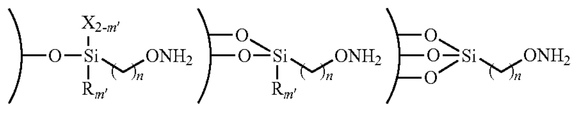

(wherein R is a $C_{1-4}$ alkyl group, X is a $C_{1-4}$ alkoxy group, m' is an integer of from 0 to 2, and n is an integer of from 1 to 12).

The $C_{1-4}$ alkyl group as R is not particularly restricted, but may, for example, be a methyl group, an ethyl group, a propyl group, an isopropyl group, a butyl group, a 2-methylpropyl group, a 1-methylpropyl group or a tert-butyl group.

R is preferably a methyl group to facilitate the after-mentioned silane coupling reaction.

The $C_{1-4}$ alkoxy group as X is not particularly restricted and may, for example, be a methoxy group, an ethoxy group, a propoxy group, an isopropoxy group, a butoxy group, a 2-methylpropyloxy group, a 1-methylpropyloxy group or a tert-butoxy group.

X is preferably a methoxy group, an ethoxy group, a propoxy group or an isopropoxy group, more preferably a methoxy group or an ethoxy group, more preferably a methoxy group to facilitate the after-mentioned silane coupling reaction.

m' is an integer of from 0 to 2 and is preferably 0 or 1 to facilitate the after-mentioned silane coupling reaction.

n is an integer of from 1 to 12 and is preferably an integer of from 3 to 12, more preferably 3 or 11 for more efficient removal of aldehydes.

The support having chemically bonded aminooxyalkyl groups is not particularly restricted but is preferably a product of a reaction (hereinafter referred to as a "silane coupling reaction") of a compound represented by the formula (1):

(1)

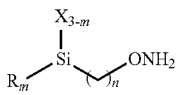

(wherein R is a $C_{1-4}$ alkyl group, X is a $C_{1-4}$ alkoxy group, m is an integer of from 0 to 2, and n is an integer of from 1 to 12) (hereinafter referred to as a "silane coupling agent") with a support having hydroxy groups on the surface.

Namely, the support having chemically bonded aminooxyalkyl groups can be produced by reacting the silane coupling agent with a support having hydroxy groups on the surface.

The definitions and preferred examples and range of R, X and n in the silane coupling agent are the same as those of R, X and n in the formula (2).

In the silane coupling agent, m is an integer of from 0 to 2 and is preferably 0 or 1 to facilitate the silane coupling reaction.

The silane coupling agent may be a commercially available product, but can be synthesized as described in Organic Preparations and Procedures International, vol. 26, 1994, 111-113, JP-A-H07-233132 or Tetrahedron Letters, Vol. 46(14), 2005, 7973-7975.

The deodorant composition of the present invention has aminooxyalkyl groups (represented as $-(CH_2)_n-ONH_2$ in the formulae (1) and (2)) as mentioned above, which may be present partly or entirely in the form of a chemically acceptable salt with an inorganic acid or an organic acid.

Such a salt is not particularly restricted but may be an inorganic salt such as a hydrochloride, a hydrobromide, a perchlorate, a silicate, a tetrafluoroborate, a hexafluorophosphate, a sulfate, a nitrate or a phosphate, or an organic salt such as acetate, citrate, fumarate, maleate, trifluoromethanesulfonate, trifluoroacetate, benzoate or p-toluene sulfonate. The salt is preferably an inorganic salt, more preferably hydrochloride in view of cost.

The amount of amioxyalkyl groups in the support having chemically bonded amioxyalkyl groups can be adjusted arbitrarily in accordance with the intended use without any particular restrictions and is preferably from 0.01 to 10 mmol/g per unit weight of the support having chemically bonded aminooxyalkyl groups.

The support is not particularly restricted and may, for example, be a polymer support or an inorganic support.

The polymer support is not particularly restricted and may, for example, be a styrene polymer (such as polystyrene or a crosslinked polystyrene), a polyolefin (such as polyethylene or polypropylene), a poly(halogenated olefin) (such as polyvinyl chloride or polytetrafluoroethylene), a nitrile polymer (such as polyacrylonitrile), a (meth)acrylate polymer (such as polymethyl methacrylate or polyethyl acrylate) or a macromolecular polysaccharide (such as cellulose, agarose or dextran).

The inorganic support is not particularly restricted and may, for example, be silica gel, alumina, zeolite, magnesia, titania, zirconia, ceria, diatomaceous earth, activated carbon, or hydroxyapatite.

The support is preferably silica gel, alumina, zeolite, magnesia, titania, zirconia, ceria, diatomaceous earth, activated carbon, cellulose or hydroxyapatite, further preferably silica gel to facilitate the silane coupling reaction.

The support preferably has hydroxy groups on the surface.

The support may be in any form without any particular restrictions and may be in the form of spheres, particles, fiber, granules, a monolithic column, hollow fiber or a membrane. It is preferably in the form of beads, a membrane, particles, granules or fiber, more preferably in the form of beads, particles or granules, for effective removal of aldehydes.

Regarding the size of the support in the form of beads, particles or granules, the average diameter is preferably from 0.1 μm to 10 mm, more preferably from 1 μm to 100 μm, in view of dispersibility in a liquid.

The support may be porous or non-porous and is preferably porous for effective removal of aldehydes.

When the support is porous, the average pore size is preferably from 1 nm to 1 μm, more preferably from 1 nm to 300 nm, for effective removal of aldehydes.

The binder resin in the deodorant composition of the present invention is not particularly restricted and may, for example, be an acrylate resin, a silicone resin, a urethan resin, a polyester resin, a melamine resin, a polypropylene resin or a fluororesin.

The binder resin is preferably an acrylate resin, a silicone resin or a urethan resin in view of adhesion to the support having chemically bonded aminooxyalkyl groups and water resistance.

The weight ratio of the support having chemically bonded aminooxyalkyl groups and the binder resin in the deodorant composition can be adjusted arbitrarily in accordance with the intended use without any particular restrictions, and the ratio of the support having chemically bonded aminooxyalkyl groups (weight):the binder resin (weight) is preferably from 1:1000 to 100:1, more preferably from 1:100 to 100:1, more preferably from 1:1.2 to 10:1.

The deodorant composition of the present invention comprises a support having chemically bonded aminooxyalkyl groups and a binder resin and may be prepared by mixing the support having chemically bonded aminooxyalkyl groups and the binder resin or by drying a deodorant suspension, which will be described later, without any particular restrictions.

The deodorant composition of the present invention may further comprise a solvent.

The solvent is not particularly restricted and may, for example, be water, ethanol, methanol, propanol, acetonitrile or the like. Among them, water is preferred for effective removal of aldehydes.

When the deodorant composition of the present invention comprises a relatively large amount of a solvent (the deodorant composition of the present invention also covers such a mixture containing a solvent), it is in the form of a suspension. Hereinafter, such a suspension will be referred to as a deodorant suspension.

The weight ratio of the sum of the support having chemically bonded aminooxyalkyl groups and the binder resin to the solvent can be adjusted arbitrarily in accordance with the intended use without any particular restrictions, and the ratio of the sum of the two (weight):the solvent (weight) is preferably 1:1000 to 1:2, more preferably from 1:100 to 1:4, more preferably from 1:50 to 1:4.

The deodorant suspension may be prepared by mixing the support having chemically bonded aminooxyalkyl groups, the binder resin and the solvent by stirring, without any particular restrictions.

The deodorant composition or the deodorant suspension may be used in any ways with no particular restrictions, for example, by bringing the deodorant composition or the deodorant suspension into contact with an odor source (emitting an aldehyde), by spraying the composition or suspension directly onto the odor source, by exposing the deodorant composition or the deodorant suspension to an atmosphere containing a malodorous substance (such as an aldehyde) or by spraying the deodorant composition or the deodorant suspension into such an atmosphere.

As the odor source, an adhesive containing an organic solvent, a building material in a new building, plywood or the like may, for example, be mentioned, though there are no particular restrictions.

The deodorant composition or the deodorant suspension can decrease the odor from an odor source by capturing the malodorous substance when brought into contact with the odor source or sprayed directly onto the odor source.

The deodorant composition or the deodorant suspension can decrease the odor of an atmosphere containing a malodorous substance by capturing the malodorous substance (such as an aldehyde) when exposed to the atmosphere or sprayed into the atmosphere.

As the malodorous substance, formaldehyde, acetaldehyde, propionaldehyde, normalbutyraldehyde, isobutyraldehyde, normalvaleraldehyde, isovaleraldehyde, hexanal, hexenal, nonenal, methyl isobutyl ketone, diacetyl, ethyl acetate, acetic acid, propionic acid, n-butyric acid, n-valeric acid, isovaleric acid, methyl mercaptan, ethyl mercaptan or the like may, for example, be mentioned, though there are no particular restrictions.

The deodorant composition or the deodorant suspension may be used in different ways with no particular restrictions, for example, as a coating on a substrate, to use the substrate having a coating of the deodorant composition or the deodorant suspension on the surface as a deodorant article.

Such a deodorant article may be prepared by applying or spraying the deodorant composition or the deodorant suspension onto a substrate.

The deodorant article can decrease the odor of an atmosphere containing a malodorous substance by capturing the malodorous substance (such as an aldehyde) when exposed to the atmosphere.

As the substrate, fiber, sheet, wallpaper, sponge, beads, wood, plywood or plasterboard may, for example, be mentioned, though there are no particular restrictions.

As the material of fiber, sheet, wallpaper or sponge, polyester, polyamide, polyacrylonitrile, polypropylene, polyethylene, polyvinyl chloride, a fluororesin, an aramid resin, a sulfone resin, rayon, acetate rayon, cotton, wool, silk, hemp, glass, carbon, ceramics, a silicone resin, a polyimide resin, natural rubber or polyurethane may, for example, be mentioned, though there are no particular restrictions.

The deodorant article may, for example, clothing, a curtain, a carpet, a wall covering, an automobile interior part or furniture may, for example, be mentioned, though there are no particular restrictions.

The amount of the deodorant composition on the substrate can be adjusted arbitrarily in accordance with the intended use without any particular restrictions, but is preferably from 0.1 to 200 $g/m^2$, more preferably from 0.5 to 75 $g/m^2$, per unit area of the substrate.

The amount of the support having chemically bonded aminooxyalkyl groups on the substrate can be adjusted arbitrarily in accordance with the intended use without any particular restrictions, but is preferably from 0.09 to 180 $g/m^2$, more preferably from 0.45 to 68 $g/m^2$, per unit area of the substrate.

EXAMPLES

Now, the present invention will be described in further detail with reference to Examples. However, it should be understood that these Examples are intended to help understand the present invention, and the present invention is by no means restricted thereto. As the reagents, commercially available products were used unless otherwise noted.

The evaluation procedure and the analytical instrument used in the Examples are described below.

<Acetaldehyde Removal Test>

A deodorant article was sealed in a 5 L Tedlar bag, and 3 L of nitrogen gas containing about 14 ppm acetaldehyde was injected. After 2 hours of standing at room temperature, the gas in the Tedlar bag was passed through a 2,4-dinitrophenyihydrazine (DNPH) cartridge column (Precep-C DNPH, manufactured by FUJIFILM Wako Pure Chemical Corporation) to adsorb the aldehyde in the gas on it. The DNPH-aldehyde condensate was eluted from the column with acetonitrile. The eluate was analyzed with a liquid chromatograph (LC-2030C Plus, manufactured by Shimadzu Corporation) to quantify the DNPH-aldehyde condensate, and the concentration of the remaining acetaldehyde in the Tedlar bag was calculated. The aldehyde removal rate [%] was calculated from the following formula.

Acetaldehyde removal rate[%]=[(Initial acetaldehyde concentration−Remaining acetaldehyde concentration)/Initial acetaldehyde concentration]×100

Synthetic Example 1

To a mixture of 19.94 g of silica gel having an average particle diameter of 4 μm (NIPGEL BY-400, manufactured by Tosoh Silica Corporation) and 173.4 g of toluene, 8.08 g of a silane coupling agent represented by the following chemical formula (1a) and 43.35 g of toluene was added dropwise in a nitrogen stream, and the resulting reaction solution was stirred at 25° C. for 120 hours. The reaction solution was filtered, and the filter cake was dried at 120° C. for 4 hours to obtain a support having chemically bonded amioxyalkyl groups (hereinafter referred to as an “aminooxy support”). The aminooxy support was found to contain 1.4 mmol/g of aminooxyalkyl groups per unit weight of the aminooxy support, by elemental analysis.

(1a)

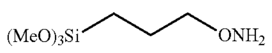

Infrared spectra (hereinafter referred to as IR spectra) of untreated silica gel (NIPGEL BY-400, manufactured by Tosoh Silica Corporation) and the aminooxy support were measured. The spectrum of the aminooxy support lacked the Si—O bending vibration peak which appeared at around 970 $cm^{-1}$ in the spectrum of the untreated silica gel. This indicates the chemical modification of hydroxy groups on the surface of the silica gel with the silane coupling agent represented by the chemical formula (1a).

Synthetic Example 2

To a mixture of 16.88 g of silica gel having an average particle diameter of 14 μm (NIPGEL BY-001, manufactured by Tosoh Silica Corporation), 44.87 g of toluene and 16.88 g of distilled water, a mixture of 5.42 of the silane coupling agent represented by the chemical formula (1a) and 22.66 g of toluene was added dropwise in a nitrogen stream, and the resulting reaction solution was heated under reflux with stirring for 4 hours. The reaction solution was filtered, and the filter cake was dried at 120° C. for 4 hours to obtain an aminooxy support. The aminooxy support was found to contain 1.5 mmol/g of aminooxyalkyl groups per unit weight of the aminooxy support, by elemental analysis.

IR spectra of untreated silica gel (NIPGEL BY-001, manufactured by Tosoh Silica Corporation) and the aminooxy support were measured. The spectrum of the aminooxy support lacked the Si—O bending vibration peak which appeared at around 970 $cm^1$ in the spectrum of the untreated silica gel. This indicates the chemical modification of hydroxy groups on the surface of the silica gel with the silane coupling agent represented by the chemical formula (1a).

Synthetic Example 3

To a mixture of 16.88 g of silica gel having an average particle diameter of 21 μm (NIPSIL NS-T, manufactured by Tosoh Silica Corporation), 45.00 g of toluene and 16.88 g of distilled water, a mixture of 5.40 g of the silane coupling agent represented by the chemical formula (1a) and 22.72 g of toluene was added dropwise in a nitrogen stream, and the resulting reaction solution was heated under reflux with stirring for 4 hours. The reaction solution was filtered, and the filter cake was dried at 120° C. for 4 hours to obtain an aminooxy support. The aminooxy support was found to contain 1.4 mmol/g of aminooxyalkyl groups per unit weight of the aminooxy support, by elemental analysis.

IR spectra of untreated silica gel (NIPSIL NS-T, manufactured by Tosoh Silica Corporation) and the aminooxy support were measured. The spectrum of the aminooxy support lacked the Si—O bending vibration peak which appeared at around 970 $cm^{-1}$ in the spectrum of the untreated silica gel. This indicates the chemical modification of hydroxy groups on the surface of the silica gel with the silane coupling agent represented by the chemical formula (1a).

Synthetic Example 4

3.05 g of silica gel having an average particle diameter of 4 μm (NIPGEL BY-400, manufactured by Tosoh Silica Corporation), 12.22 g of toluene, 0.46 g of distilled water and 0.90 g of a silane coupling agent represented by the following chemical formula (1 b) were mixed and heated under reflux in a nitrogen stream with stirring for 4 hours. The resulting reaction solution was filtered, and the filter cake was dried at 120° C. for 4 hours to obtain an aminooxy support. The aminooxy support was found to contain 1.1 mmol/g of aminooxyalkyl groups per unit weight of the aminooxy support, by elemental analysis.

(1b)

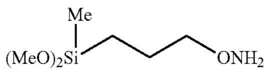

IR spectra of untreated silica gel (NIPGEL BY-400, manufactured by Tosoh Silica Corporation) and the aminooxy support were measured. The spectrum of the aminooxy support lacked the Si—O bending vibration peak which appeared at around 970 $cm^{-1}$ in the spectrum of the untreated silica gel. This indicates the chemical modification of hydroxy groups on the surface of the silica gel with the silane coupling agent represented by the chemical formula (1b).

Synthetic Example 5

2.44 g of silica gel having an average particle diameter of 4 μm (NIPGEL BY-400, manufactured by Tosoh Silica Corporation), 9.78 g of toluene, 0.37 g of distilled water and 0.95 g of a silane coupling agent represented by the following chemical formula (1c) were mixed and heated under reflux in a nitrogen stream with stirring for 4 hours. The resulting reaction solution was filtered, and the filter cake was dried at 120° C. for 4 hours to obtain an aminooxy support. The aminooxy support was found to contain 0.9 mmol/g of aminooxyalkyl groups per unit weight of the aminooxy support, by elemental analysis.

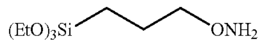

(1c)

IR spectra of untreated silica gel (NIPGEL BY-400, manufactured by Tosoh Silica Corporation) and the aminooxy support were measured. The spectrum of the aminooxy support lacked the Si—O bending vibration peak which appeared at around 970 $cm^{-1}$ in the spectrum of the untreated silica gel. This indicates the chemical modification of hydroxy groups on the surface of the silica gel with the silane coupling agent represented by the chemical formula (1c).

Synthetic Example 6

1.83 g of silica gel having an average particle diameter of 4 μm (NIPGEL BY-400, manufactured by Tosoh Silica Corporation), 7.32 g of toluene, 0.27 g of distilled water and 0.93 g of a silane coupling agent represented by the following chemical formula (1d) were mixed and heated under reflux in a nitrogen stream with stirring for 4 hours. The resulting reaction solution was filtered, and the filter cake was dried at 120° C. for 4 hours to obtain an aminooxy support. The aminooxy support was found to contain 0.8 mmol/g of aminooxyalkyl groups per unit weight of the aminooxy support, by elemental analysis.

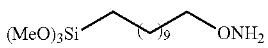

(1d)

IR spectra of untreated silica gel (NIPGEL BY-400, manufactured by Tosoh Silica Corporation) and the aminooxy support were measured. The spectrum of the aminooxy support lacked the Si—O bending vibration peak which appeared at around 970 $cm^{-1}$ in the spectrum of the untreated silica gel. This indicates the chemical modification of hydroxy groups on the surface of the silica gel with the silane coupling agent represented by the chemical formula (1d).

Synthetic Example 7

3.05 g of coconut shell activated carbon powder (Shirasagi M, manufactured by Osaka Gas Chemicals Co., Ltd.), 12.30 of toluene, 0.45 g of distilled water and 0.97 g of the silane coupling agent represented by the chemical formula (1a) were mixed and heated under reflux in a nitrogen stream with stirring for 4 hours. The resulting reaction solution was filtered, and the filter cake was dried at 120° C. for 4 hours to obtain an aminooxy support. The aminooxy support was found to contain 1.4 mmol/g of aminooxyalkyl groups per unit weight of the aminooxy support, by elemental analysis.

Synthetic Example 8

3.05 g of wood activated powder (CARBORAFFIN, manufactured by Osaka Gas Chemicals Co., Ltd.), 12.24 of toluene, 0.46 g of distilled water and 0.98 g of the silane coupling agent represented by the chemical formula (1a) were mixed and heated under reflux in a nitrogen stream with stirring for 4 hours. The resulting reaction solution was filtered, and the filter cake was dried at 120° C. for 4 hours to obtain an aminooxy support. The aminooxy support was found to contain 1.6 mmol/g of aminooxyalkyl groups per unit weight of the aminooxy support, by elemental analysis.

Example 1

0.20 g of the aminooxy support obtained in Synthetic Example 1, 0.24 g of an acrylate binder resin (FICOAT 70K, manufactured by Daiwa Chemical Industries Co., Ltd.) and 9.56 g of distilled water were mixed in a polyethylene vessel to obtain a deodorant composition (a deodorant suspension).

750 μL (0.75 g) of the deodorant composition (deodorant suspension) was applied onto a 10 cm×10 cm 100 percent polyester cloth and dried in a hot-air dryer (DRJ433DA, manufactured by the ADVANTECH group) at 150° C. for 3 minutes to obtain a deodorant article having a coating of the deodorant composition.

The deodorant article was washed with water 5 times in accordance with the washing durability test (JIS L0217 103).

The deodorant article was assessed by the aldehyde removal test before and after the washings.

Example 2

A deodorant composition (deodorant suspension) and a deodorant article were prepared and assessed in the same manner as in Example 1 except that 0.24 g of the acrylate binder resin (FICOAT 70K, manufactured by Daiwa Chemical Industries Co., Ltd.) was replaced by 0.24 g of a silicone binder resin (S-200L, manufactured by Daiwa Chemical Industries Co., Ltd.), Example 3

A deodorant composition (deodorant suspension) and a deodorant article were prepared and assessed in the same manner as in Example 1 except that 0.24 g of the acrylate binder resin (FICOAT 70K, manufactured by Daiwa Chemical Industries Co., Ltd.) was replaced by 0.24 g of a urethan binder resin (U-30NP, manufactured by Daiwa Chemical Industries Co., Ltd.).

Example 4

A deodorant composition (deodorant suspension) and a deodorant article were prepared and assessed in the same manner as in Example 1 except that the 10 cm×10 cm 100 percent polyester cloth was replaced by a 10 cm×10 cm 100 percent cotton cloth.

Example 5

A deodorant composition (deodorant suspension) and a deodorant article were prepared and assessed in the same manner as in Example 1 except that the amount of the coating of the deodorant composition (deodorant suspension) was changed from 750 μL (0.75 g) to 250 μL (0.25 g).

Example 6

A deodorant composition (deodorant suspension) and a deodorant article were prepared and assessed in the same manner as in Example 1 except that the amount of the acrylate binder resin (FICOAT 70K, manufactured by Daiwa Chemical Industries Co., Ltd.) was changed from 0.24 g to 0.08 g, and the amount of distilled water was changed from 9.56 g to 9.72 g.

Example 7

A deodorant composition (deodorant suspension) and a deodorant article were prepared and assessed in the same manner as in Example 1 except that the amount of the acrylate binder resin (FICOAT 70K, manufactured by Daiwa Chemical Industries Co., Ltd.) was changed from 0.24 g to 0.02 g, and the amount of distilled water was changed from 9.56 g to 9.78 g.

Example 8

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 2.

Example 9

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 3.

Example 10

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 4.

Example 11

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 5.

Example 12

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 6.

Example 13

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 7.

Example 14

A deodorant composition (deodorant suspension) and a deodorant article were prepared and assessed in the same manner as in Example 1 except that 0.20 g of the aminooxy support obtained in Synthetic Example 1 was replaced by 0.20 g of the aminooxy support obtained in Synthetic Example 8.

Comparative Example 1

A deodorant composition (deodorant suspension) and a deodorant article were prepared and assessed in the same manner as in Example 4 except that 0.24 g of the acrylate binder resin (FICOAT 70K, manufactured by Daiwa Chemical Industries Co., Ltd.) was not added, and the amount of distilled water was changed from 9.56 g to 9.80 g.

Comparative Example 2

A deodorant composition (deodorant suspension) and a deodorant article were prepared and assessed in the same manner as in Example 4 except that 0.20 g of the aminooxy support was not added, and the amount of distilled water was changed from 9.56 g to 9.76 g.

Comparative Example 3

A deodorant article was prepared and assessed in the same manner as in Example 4 except that 10.0 g of the deodorant composition (deodorant suspension) prepared by mixing 0.20 g of aminooxy support, 0.24 g of the acrylate binder resin (FICOAT 70K, manufactured by Daiwa Chemical Industries Co., Ltd.) and 9.56 g of distilled water was replaced by 10.0 g of 3 wt % aminooxyacetic acid aqueous solution.

Comparative Example 4

A deodorant article was prepared and assessed in the same manner as in Example 4 except that 10.0 g of the deodorant composition (deodorant suspension) prepared by mixing 0.20 g of aminooxy support, 0.24 g of the acrylate binder resin (FICOAT 70K, manufactured by Daiwa Chemical Industries Co., Ltd.) and 9.56 g of distilled water was replaced by 10.0 g of 3 wt % adipic dihydrazide aqueous solution.

Comparative Example 5

A deodorant composition (deodorant suspension) and a deodorant article were prepared and assessed in the same manner as in Example 1 except that 0.24 g of the acrylate binder resin (FICOAT 70K, manufactured by Daiwa Chemical Industries Co., Ltd.) was not added, and the amount of distilled water was changed from 9.56 g to 9.80 g.

Comparative Example 6

A deodorant article was prepared and assessed in the same manner as in Example 1 except that 10.0 g of the deodorant composition (deodorant suspension) prepared by mixing 0.20 g of an aminooxy support, 0.24 g of an acrylate binder resin (FICOAT 70K, manufactured by Daiwa Chemical Industries Co., Ltd.) and 9.56 g of distilled water was replaced by 10.0 g of a deodorant composition (deodorant suspension) prepared by mixing 0.20 g of a commercial inorganic aldehyde scavenger (KESMON NS750, manufactured by TOAGOSEI Co., LTD.), 0.24 g of an acrylate binder resin (FICOAT 70K, manufactured by Daiwa Chemical Industries Co., Ltd.) and 9.56 g of distilled water.

Comparative Example 7

A deodorant article was prepared and assessed in the same manner as in Example 1 except that 10.0 g of the deodorant composition (deodorant suspension) prepared in Example 1 by mixing 0.20 g of an aminooxy support, 0.24 g of an acrylate binder resin (FICOAT 70K, manufactured by Daiwa Chemical Industries Co., Ltd.) and 9.56 g of distilled water was replaced by 10.0 g of a deodorant composition (deodorant suspension) prepared by mixing 0.20 g of a commercial inorganic aldehyde scavenger (KESMON NS750, manufactured by TOAGOSEI Co., LTD.), 0.08 g of an acrylate binder resin (FICOAT 70K, manufactured by Daiwa Chemical Industries Co., Ltd.) and 9.72 g of distilled water.

Comparative Example 8

A deodorant article was prepared and assessed in the same manner as in Example 6 except that 10.0 g of the deodorant composition (deodorant suspension) prepared by mixing 0.20 g of an aminooxy support, 0.24 g of an acrylate binder resin (FICOAT 70K, manufactured by Daiwa Chemical Industries Co., Ltd.) and 9.56 g of distilled water was replaced by a deodorant composition (deodorant suspension) prepared by mixing 0.20 g of unmodified silica gel (NIPSIL BY-400, manufactured by Tosoh Silica Corporation), 0.24 g of an acrylate binder resin (FICOAT 70K, manufactured by Daiwa Chemical Industries Co., Ltd.) and 9.56 g of distilled water.

The results of Examples 1 to 14 are shown in Table 1, and the results of Comparative Examples 1 to 8 are shown in Table 2. It is clear from Tables 1 and 2 that the deodorant compositions of the present invention were more waterproof than conventional deodorant compositions.

TABLE 1

| | | Amiooxy support | | Binder resin | | Amount of | Acetaldehyde removal rate [%] | | |
|---|---|---|---|---|---|---|---|---|---|
| Ex. | Cloth Kind | Kind | Amount [wt %] | Kind | Amount [wt %] | coating [g/m$^2$] | Before washings | After one washing | After 5 washings |
| Ex. 1 | Polyester | Synthetic Ex. 1 Compound (1a) | 2 | Acrylate | 2.4 | 75 | 100 | 100 | 100 |
| Ex. 2 | Polyester | Synthetic Ex. 1 Compound (1a) | 2 | Silicone | 2.4 | 75 | 100 | 100 | 100 |
| Ex. 3 | Polyester | Synthetic Ex. 1 Compound (1a) | 2 | Urethan | 2.4 | 75 | 100 | 100 | 100 |
| Ex. 4 | Cotton | Synthetic Ex. 1 Compound (1a) | 2 | Acrylate | 2.4 | 75 | 100 | 100 | 100 |
| Ex. 5 | Polyester | Synthetic Ex. 1 Compound (1a) | 2 | Acrylate | 2.4 | 25 | 100 | 69 | 27 |
| Ex. 6 | Polyester | Synthetic Ex. 1 Compound (1a) | 2 | Acrylate | 0.8 | 75 | 100 | 100 | 99 |
| Ex. 7 | Polyester | Synthetic Ex. 1 Compound (1a) | 2 | Acrylate | 0.2 | 75 | 100 | 100 | 88 |
| Ex. 8 | Polyester | Synthetic Ex. 2 Compound (1a) | 2 | Acrylate | 2.4 | 75 | 100 | 100 | 88 |
| Ex. 9 | Polyester | Synthetic Ex. 3 Compound (1a) | 2 | Acrylate | 2.4 | 75 | 100 | 82 | 50 |
| Ex. 10 | Polyester | Synthetic Ex. 4 Compound (1b) | 2 | Acrylate | 2.4 | 75 | 100 | 100 | 100 |
| Ex. 11 | Polyester | Synthetic Ex. 5 Compound (1c) | 2 | Acrylate | 2.4 | 75 | 100 | 100 | 100 |
| Ex. 12 | Polyester | Synthetic Ex. 6 Compound (1d) | 2 | Acrylate | 2.4 | 75 | 100 | 100 | 33 |
| Ex. 13 | Polyester | Synthetic Ex. 7 Compound (1a) | 2 | Acrylate | 2.4 | 75 | 83 | 56 | 41 |
| Ex. 14 | Polyester | Synthetic Ex. 8 Compound (1a) | 2 | Acrylate | 2.4 | 75 | 100 | 75 | 73 |

TABLE 2

| | | Amiooxy support | | Binder resin | | Amount of | Acetaldehyde removal rate [%] | | |
|---|---|---|---|---|---|---|---|---|---|
| Ex. | Cloth Kind | Kind | Amount [wt %] | Kind | Amount [wt %] | coating [g/m$^2$] | Before washings | After one washing | After 5 washings |
| Comparative Ex. 1 | Cotton | Synthetic Ex. 1 Compound (1a) | 2 | None | 0 | 75 | 100 | 0 | 0 |

TABLE 2-continued

| | | Amiooxy support | | Binder resin | | Amount of | Acetaldehyde removal rate [%] | | |
|---|---|---|---|---|---|---|---|---|---|
| Ex. | Cloth Kind | Kind | Amount [wt %] | Kind | Amount [wt %] | coating [g/m$^2$] | Before washings | After one washing | After 5 washings |
| Comparative Ex. 2 | Cotton | None | 0 | Acrylate | 2.4 | 75 | 0 | 0 | 0 |
| Comparative Ex. 3 | Cotton | Aminooxyacetic acid | 3 | None | 0 | 75 | 100 | 0 | 0 |
| Comparative Ex. 4 | Cotton | Adipic dihydrazide | 3 | None | 0 | 75 | 55 | 0 | 0 |
| Comparative Ex. 5 | Polyester | Synthetic Ex. 1 Compound (1a) | 2 | None | 0 | 75 | 100 | 0 | 0 |
| Comparative Ex. 6 | Polyester | KESMON NS750 | 2 | Acrylate | 2.4 | 75 | 80 | 34 | 13 |
| Comparative Ex. 7 | Polyester | KESMON NS750 | 2 | Acrylate | 0.8 | 75 | 81 | 34 | 8 |
| Comparative Ex. 8 | Polyester | Silica gel | 2 | Acrylate | 2.4 | 75 | 7 | 6 | 5 |

The entire disclosure of Japanese Patent Application No. 2021-054339 filed on Mar. 26, 2021 including specification, claims and summary is incorporated herein by reference in its entirety.

The invention claimed is:

1. A deodorant composition comprising a support having chemically bonded aminooxyalkyl groups and a binder resin, wherein the support having chemically bonded aminooxyalkyl groups has a structure represented by the following formula (2a), (2b), or (2c);

(2a)

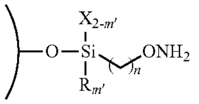

(2b)

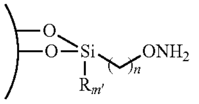

(2c)

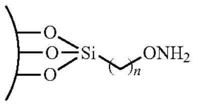

wherein R is a $C_{1-4}$ alkyl group, X is a $C_{1-4}$ alkoxy group, m' is an integer of from 0 to 2, and n is an integer of from 1 to 12.

2. The deodorant composition according to claim 1, wherein when present R is a methyl group, and when present X is a methoxy group, an ethoxy group, a propoxy group or an isopropoxy group.

3. The deodorant composition according to claim 1, wherein n is 3 or 11.

4. The deodorant composition according to claim 1, wherein the structure represented by the formulas (2a), (2b), or (2c) is a product of a reaction of a compound represented by the following formula (1) with an inorganic support or polymer support having hydroxy groups on the surface:

(1)

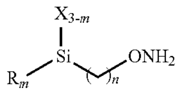

wherein R when present is a $C_{1-4}$ alkyl group, X when present is a $C_{1-4}$ alkoxy group, m is an integer of from 0 to 2, and n is an integer of from 1 to 12, and wherein the reaction is carried out in toluene.

5. The deodorant composition according to claim 4, wherein R is a methyl group, and X is a methoxy group, an ethoxy group, a propoxy group or an isopropoxy group.

6. The deodorant composition according to claim 4, wherein n is 3 or 11.

7. The deodorant composition according to claim 4, wherein the inorganic support is silica gel, alumina, zeolite, magnesia, titania, zirconia, ceria, diatomaceous earth, activated carbon, or hydroxyapatite.

8. The deodorant composition according to claim 4, wherein the inorganic support is silica gel.

9. The deodorant composition according to claim 1, wherein the binder resin is an acrylate resin, a silicone resin or a urethan resin.

10. A method for removing an aldehyde, which comprises exposing the deodorant composition of claim 1 to air containing an aldehyde to bring the aldehyde into contact with the deodorant composition.

11. A deodorant article comprising the deodorant composition of claim 1 and a substrate having the deodorant composition on the surface, wherein the substrate is fiber, sheet wallpaper, sponge, beads, wood, plywood or plasterboard.

12. A method for removing an aldehyde, which comprises exposing the deodorant article of claim 11 to air containing an aldehyde to bring the aldehyde into contact with the deodorant article.

* * * * *